United States Patent [19]

Hardeman

[11] Patent Number: 5,944,681
[45] Date of Patent: Aug. 31, 1999

[54] TOPICAL MEDICATION COVERINGS

[76] Inventor: Carol Hardeman, 6401 S. Laflin, Chicago, Ill. 60636

[21] Appl. No.: 09/057,886
[22] Filed: Apr. 9, 1998
[51] Int. Cl.[6] ...................................................... A61F 13/00
[52] U.S. Cl. ............................................................ 602/60
[58] Field of Search ............................... 602/58, 20, 23, 602/60, 61

[56] References Cited

U.S. PATENT DOCUMENTS

| 4,905,681 | 3/1990 | Glascock | 128/155 |
| 4,975,984 | 12/1990 | Sting | 2/114 |
| 5,437,621 | 8/1995 | Andrews et al. | 602/42 |
| 5,501,661 | 3/1996 | Cartmell et al. | 602/58 |
| 5,586,971 | 12/1996 | Newman | 602/58 |

Primary Examiner—Richard J. Apley
Assistant Examiner—Kelvin Hart
Attorney, Agent, or Firm—Henderson & Sturm

[57] ABSTRACT

Topical medication coverings 10 including a cruciform shaped upper torso cover member 20, a pi shaped lower torso cover member 30 and a winged T-shaped foot cover member 40 wherein all of the differently configured cover members 20, 30, and 40 are provided with a plurality of panels and each cover member 20, 30 and 40 may be folded about a centerline 50 to form mirror image halves.

4 Claims, 2 Drawing Sheets

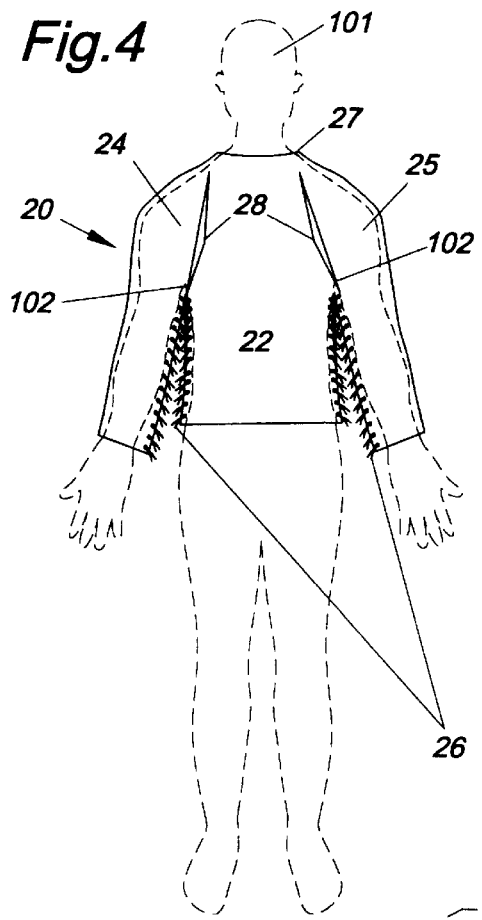
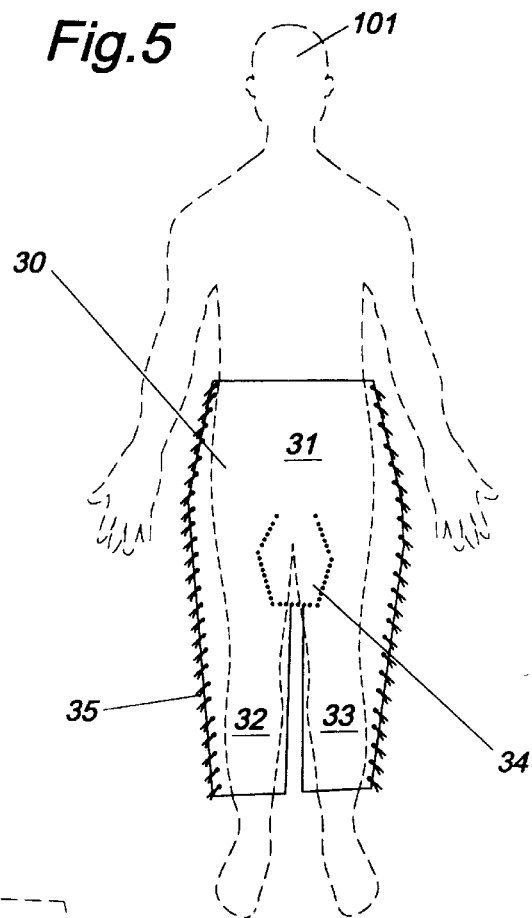
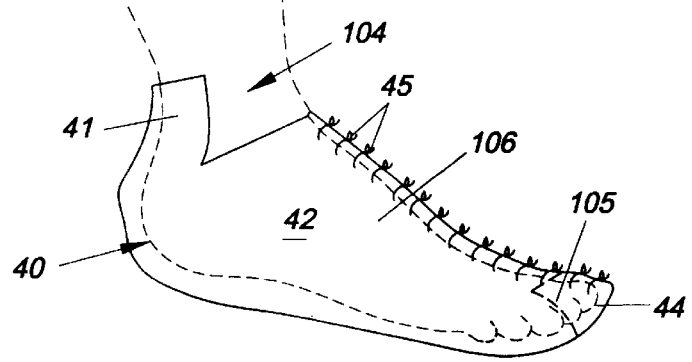

TOPICAL MEDICATION COVERINGS

CROSS REFERENCE TO RELATED APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

The present invention relates to the field of medical dressings in general, and in particular to a new type of topical medication coverings.

2. Description of Related Art

As can be seen by reference to the following U.S. Pat. Nos. 4,905,681; 5,437,621; 5,501,661; and 5,586,971, the prior art is replete with numerous and diverse medical dressings, bandages and protective coverings.

While all of the aforementioned prior art constructions are more than adequate for the basic purpose and function for which they have been specifically designed, they are uniformly deficient with respect to their failure to provide a simple, efficient, and practical way to cover topical medications on a patient's torso and extremities.

The conventional manner of covering topical medications is to employ a wrap to form a body shape from strips of material that are connected together by tape. Not only is this procedure time consuming, but it also entails a great deal of patient involvement which in retrospect is extremely impractical.

As a consequence of the foregoing situation, there has existed a longstanding need among health care givers for a new and improved method of covering topical medications with minimal rubbing action of the treated skin by the covering fabric, and the provision of such a construction is a stated objective of the present invention.

BRIEF SUMMARY OF THE INVENTION

Briefly stated, the topical medication coverings that form the basis of the present invention comprises in general a series of one piece coverings that are foldable about a centerline to form mirror image cover halves that are designed to envelope specific portions of a patient's anatomy.

As will be explained in greater detail further on in the specification, the topical medical coverings include an upper torso cover unit, a lower torso cover unit, and a foot cover unit. All of the cover units have mirror image halves foldable about a centerline and are provided with securing elements to join selected portions of the external periphery of each cover unit together.

In addition, the upper torso unit has a generally cruciform configuration, the lower torso unit has a generally π shaped configuration and the foot unit has a winged T-shaped configuration.

BRIEF DESCRIPTION OF THE SEVERAL VIEWS OF THE DRAWINGS

These and other attributes of the invention will become more clear upon a thorough study of the following description of the best mode for carrying out the invention, particularly when reviewed in conjunction with the drawings, wherein:

FIG. 4 shows the upper torso unit disposed on a patient's upper torso;

FIG. 5 shows the lower torso unit disposed on a patient's lower torso; and

FIG. 6 shows the foot unit disposed on a patient's foot.

DETAILED DESCRIPTION OF THE INVENTION

Figure 1:
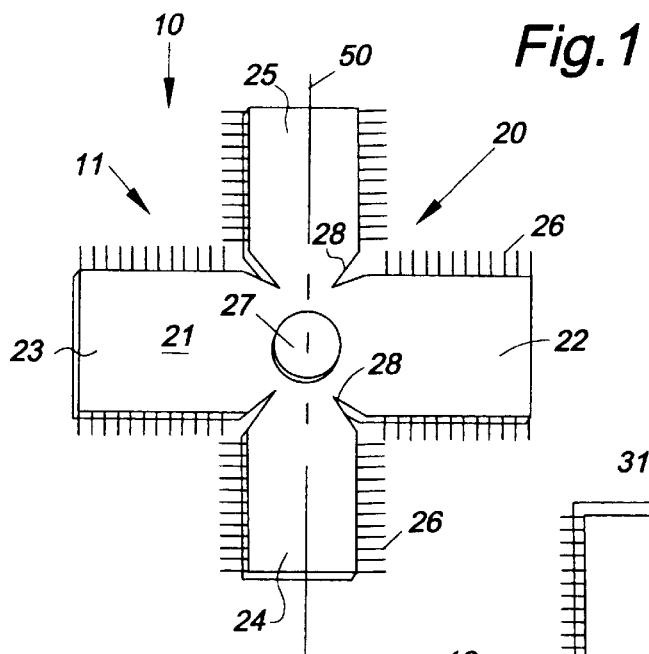
FIG. 1 is a top plan view of the upper torso cover unit.

As can be seen by reference to the drawings, and in particularly to FIG. 1, the topical medication coverings that form the basis of the present invention is designated generally by the reference number 10. The coverings 10 comprise in general an upper torso cover unit 11, a lower torso cover unit 12, and a foot cover unit 13. These cover units will now be described in seriatim fashion.

As can best be seen by reference to FIGS. 1 and 4, the upper torso cover unit 11 comprises a generally flat cruciform shaped upper torso cover member 20 fabricated from a single sheet of hypo-allergenic soft cotton fabric 21.

The upper torso cover member 20 further includes relatively wide diametrically opposed front 22 and back 23 panels and relatively narrow diametrically opposed left arm 24 and right arm 25 panels which form the generally cruciform configuration of the upper torso cover member 20.

In addition, the opposite sides of all the generally rectangular panels 22, 23, 24, and 25 are provided with securing elements 26 such that the front panel 22 can be attached to the back panel 23 and the opposite sides of each of the arm panels 24 and 25 can be attached to one another.

Furthermore, as shown in FIGS. 1 and 4, an enlarged central aperture 27 is provided intermediate the juncture of the panels 22, 23, 24, and 25 to provide an opening for the patient's head 101 and angled slits 28 are provided at the juncture of the panels 22 through 25 such that the upper torso cover member 20 is open in the vicinity of the patient's armpits 102 which is the one area that affords the greatest opportunity for fabric on fabric rubbing contact by prior art body wrappings.

Figure 2:
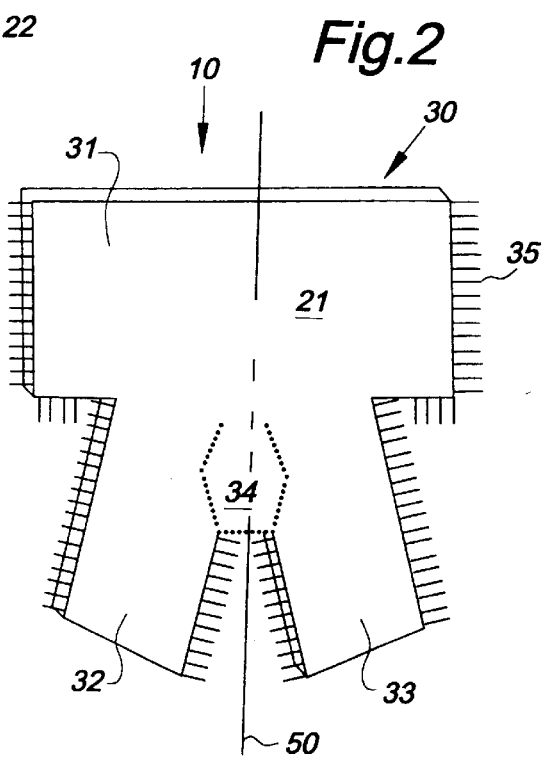
FIG. 2 is a top plan view of the lower torso cover unit.

Turning now to FIGS. 2 and 5, it can be seen that the lower torso cover unit 12 comprises a generally flat pi (π) shaped lower torso cover member 30 also fabricated from a single sheet of hypo allergenic soft cotton fabric 21.

The lower torso cover member 30 comprises a generally rectangular lower trunk panel 31 and left leg 32 and right leg 33 panels extending downwardly at an angle from the lower portion of the lower trunk panel 31. The upper portion of each of the leg panels 32, 33 is spaced inwardly from the sides of the lower trunk panel 31.

In addition, the lower torso cover member 30 includes a crotch flap 34 formed at the juncture of the leg panels 32 and 33. The opposite sides of each of the leg panels 32, 33 and the opposite sides of the lower trunk panel 31, as well as the bottom portion of the lower trunk panel 31 are provided with securing elements 35 for forming the lower torso cover member 30 into a pants style covering.

Figure 3:
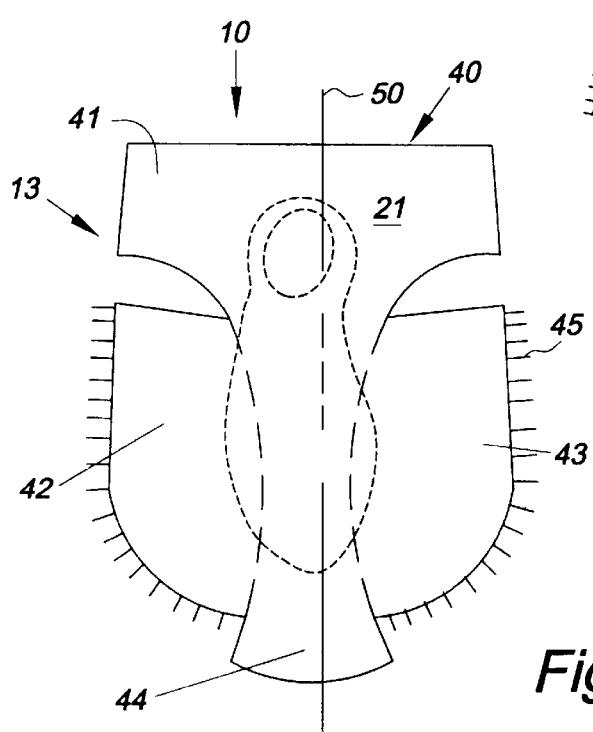
FIG. 3 is a top plan view of the foot cover unit.

Turning now to FIGS. 3 and 6, it can be seen that the foot cover unit 13 comprises a generally flat winged T-shape foot cover member 40 fabricated from a single sheet of hypo-allergenic soft cotton fabric.

As can best be seen by reference to FIG. 3, the foot cover member 40 has an upper cross arm panel 41 a pair of intermediate wing panels 42, 43 and a lower stem panel 44 wherein the outer periphery of the wing panels 42, 43 are provided with securing elements 45 for joining the wing panels together.

As shown in FIG. 6, the cross-arm panel 41 partially encircles a patient's ankle 104 whereas the stem panel 44 covers the patient's toes 105 and the wing panels 43, 43 envelope the user's foot 106 and captively engage the lower stem panel 44.

At this point, it should be apparent that all of the cover units 11, 12 and 13 share a number of common characteristics. First of all, each of the cover units 11, 12 and 13 are fabricated from a single sheet of material 21. In addition, each cover unit is configured to form mirror image halves about a vertical centerline, and the securing elements 26 are provided to join portions of the same panel or opposed panels to loosely encircle a portion of the patient's body to both cover topical medication and minimize the fabric to fabric contact of the cover unit.

Although only an exemplary embodiment of the invention has been described in detail above, those skilled in the art will readily appreciate that many modifications are possible without materially departing from the novel teachings and advantages of this invention. Accordingly, all such modifications are intended to be included within the scope of this invention as defined in the following claims.

In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooded parts together, whereas, a screw employs a helical surface, in the environment of fastening wooden parts, a nail and a screw may be equivalent structures.

I claim:

1. Topical medication covering including a contoured cover unit dimensioned to cover a specific portion of a patient's body wherein the cover unit comprises:

a single sheet of hypo-allergic material having a plurality of panels wherein the cover unit has at least one pair of panels provided with securing elements to connect said at least one pair of panels together to envelope a portion of a patient's body; and, wherein the cover unit is configured to form two mirror image halves about a centerline and including a lower torso cover unit including a generally pi shaped lower torso cover member wherein the lower torso cover member comprises a lower trunk panel and a pair of leg panels depending downwardly from said lower trunk panel.

2. The covering as in claim 1 wherein said leg panels are joined together and a crotch flat is provided at the juncture of the leg panels.

3. Topical medication covering including a contoured cover unit dimensioned to cover a specific portion of a patient's body wherein the cover unit comprises:

a single sheet of hypo-allergenic material having a plurality of panels wherein the cover unit has at least one pair of panels provided with securing elements to connect said at least one pair of panels together to envelope a portion of a patient's body; and, wherein the cover unit is configured to form two mirror image halves about a centerline and including a foot cover unit including a generally winged T-shaped foot cover member.

4. The coverings as in claim 3 wherein said foot cover member is provided with an upper cross-arm panel, a lower stem panel, and a pair of intermediate wing panels.

\* \* \* \* \*